United States Patent [19]

Clemens et al.

[11] Patent Number: 5,281,623

[45] Date of Patent: Jan. 25, 1994

[54] METHOD FOR TREATING INFLAMMATION

[75] Inventors: James A. Clemens, Indianapolis; Jill A. Panetta, Zionsville, both of Ind.

[73] Assignee: Eli Lilly and Company, Indianapolis, Ind.

[21] Appl. No.: 572,288

[22] Filed: Aug. 27, 1990

[51] Int. Cl.5 .................. A61K 31/13; A61K 31/22; A61K 31/135; A61K 31/225

[52] U.S. Cl. .................. 514/654; 514/546; 514/547; 514/655; 514/825; 514/886

[58] Field of Search .............. 514/649, 886, 546, 547, 514/654, 655, 825, 886

[56] References Cited

U.S. PATENT DOCUMENTS

| | | | |
|---|---|---|---|
| 3,043,774 | 7/1962 | Coffield | 252/51.5 |
| 3,305,483 | 2/1967 | Coffield | 252/42.4 |
| 3,489,684 | 1/1970 | O'Shea | 252/51.5 |
| 3,792,170 | 2/1974 | Shen et al. | 424/303 |
| 3,809,761 | 5/1974 | Lerner | 424/330 |
| 3,994,828 | 11/1976 | Zaffaroni | 252/404 |
| 4,116,930 | 9/1978 | Dexter et al. | 260/45.8 N |
| 4,128,664 | 12/1978 | Moore | 424/324 |
| 4,532,356 | 7/1985 | Everly et al. | 568/315 |
| 4,708,966 | 11/1987 | Loomans et al. | 514/689 |
| 4,829,061 | 5/1989 | Wolf et al. | 514/218 |
| 4,948,813 | 8/1990 | Wilkerson | 514/648 |
| 4,959,503 | 9/1990 | Connor et al. | 564/265 |
| 5,002,946 | 3/1991 | Manara et al. | 514/230.8 |
| 5,011,928 | 4/1991 | Venero et al. | 544/373 |
| 5,023,378 | 6/1991 | Dowle et al. | 564/340 |
| 5,036,157 | 7/1991 | Kneen et al. | 562/623 |
| 5,039,805 | 8/1991 | Alig et al. | 546/224 |
| 5,087,743 | 2/1992 | Janssen et al. | 562/466 |
| 5,171,882 | 12/1992 | Gapinski | 562/460 |

FOREIGN PATENT DOCUMENTS

| | | |
|---|---|---|
| 42589 | 12/1981 | European Pat. Off. |
| 117033 | 8/1984 | European Pat. Off. |
| 132880 | 2/1985 | European Pat. Off. |
| 329464 | 8/1985 | European Pat. Off. |
| 233762 | 8/1987 | European Pat. Off. |
| 273451 | 7/1988 | European Pat. Off. |
| 290122 | 11/1988 | European Pat. Off. |
| 308157 | 3/1989 | European Pat. Off. |
| 84/00545 | 2/1984 | PCT Int'l Appl. |
| 1405767 | 9/1975 | United Kingdom |
| 1446781 | 8/1976 | United Kingdom |
| 1557622 | 12/1979 | United Kingdom |
| 2146529 | 4/1985 | United Kingdom |
| 2169807A | 7/1986 | United Kingdom |

OTHER PUBLICATIONS

*Chemical Abstracts*, 74, 96312e (1971).
*Derwent Abstracts*, 339971-B (abstracting JA-721730-6-R) (1972).
*Derwent Abstracts*, 20,547 (1966).
*Chemical Abstracts*, 73, 86385w (1970).
*Chemical Abstracts*, 66, 16925d (1967).
*Chemical Abstracts*, 109, 129047u (1988).
*Chemical Abstracts*, 78, 132326f (1973).
*Chemical Abstracts*, 74, 40916n (1971).
*Chemical Abstracts*, 97, 200429m (1982).
*Chemical Abstracts*, 88, 38847m (1978).
*Chemical Abstracts*, 88, 192135j (1978).
*Chemical Abstracts*, 95, 82029q (1981).
*Chemical Abstracts*, 76, 73628q (1972).
*Chemical Abstracts*, 77, 141203v (1972).
*Chemical Abstracts*, 91, 212411p (1979).
*Chemical Abstracts*, 100, 35563w (1984).
*Chemical Abstracts*, 107, 42468s (1987).
*Derwent Abstracts* 84-076585/13 (1984).
*Derwent Abstracts* 900308/50 (1979).
*Derwent Abstracts* 88-193658/28 (1988).
*Chemical Abstracts*, 109, 110014j (1988).
*Derwent Abstracts* 87-076373/11 (1987).
*Derwent Abstracts* 87-112951/16 (1987).
Patent Abst. of Japan, vol. 12, No. 467 (C-550) [3314] (1988).
Patent Abst of Japan, vol. 10, No. 287 (C-375) [2343] (1986).

Primary Examiner—Frederick E. Waddell
Assistant Examiner—Kimberly R. Jordan
Attorney, Agent, or Firm—Douglas J. Taylor; Leroy Whitaker

[57] ABSTRACT

Provided are methods of treating inflammation, arthritis and muscular dystrophy and preventing ischemia-induced cell damage employing certain phenol and benzamide compounds.

14 Claims, No Drawings

METHOD FOR TREATING INFLAMMATION

BACKGROUND OF THE INVENTION

This invention provides a method of treating inflammatory conditions, ameliorating ischemia-induced cell damage and treating muscular dystrophy in mammals.

Mammals, both humans and animals, are known to suffer form various conditions involving inflammation with concomitant swelling, tenderness, decreased mobility, pain, and fever. While a number of anti-inflammatory agents are effective in the symptomatic treatment of such inflammatory conditions as rheumatoid arthritis, rheumatoid spondylitis, osteoarthritis, degenerative joint diseases, and the like, many such agents have a number of undesirable side effects, such as gastric irritation and the like.

The etiology and pathogenesis of rheumatic and arthritic diseases remain obscure. Meanwhile, the need continues for safer, better calibrated drugs which will slow the process and alleviate the symptoms of inflammatory diseases. For example, in rheumatoid arthritis, any agent which reduces the inflammation is important in lessening or delaying the development of crippling.

A variety of therapeutic approaches have also been tried in order to prevent ischemia-induced cell damage. Such approaches have not provided a totally satisfactory method for ameliorating ischemia-induced cell damage to date.

Finally, a variety of therapeutic approaches have also been employed to treat muscular dystrophy in mammals. Again, to date none of these approaches has proven totally satisfactory.

It is an object of this invention to provide a new method for treating inflammatory conditions, and slowing the development of arthritic conditions, which method comprises administering a compound selected from among certain phenols and benzamides of the general formula

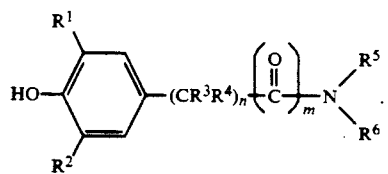

It is a further object of this invention to provide a new method of preventing ischemia-induced cell damage in mammals, which method comprises administering a compound selected from among certain phenols of the general formula set forth above.

Yet another object of this invention is to provide a new method for treating muscular dystrophy in mammals, which method comprises administering a compound selected form among certain phenols of the general formula set forth above to a mammal having muscular dystrophy.

The objects of the present invention employ certain phenols and benzamides of the general formula

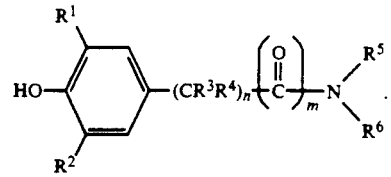

Such compounds are known in the art and have been found to possess various utilities.

U.S. Pat. No. 3,305,483 discloses that certain phenols of the above formula can be used as an antioxidant for various substances such as gasoline, diesel fuel, heating oil, lubricating oil, asphalt, petroleum wax and high molecular weight hydrocarbon polymers. *Chemical Abstracts*, 97, 200429m (1982) teaches that 4-(2-dimethylaminoethyl)-2,6-di-t-butylphenol can be used as an antioxidant for jet aircraft fuel. European Patent Application 42,589 describes the use of various of the above phenols as antioxidants for polymeric norbornene type materials.

*Chemical Abstracts*, 88, 38847m (1978) discloses that 2,6-di-t-butyl-4-[N,N-bis(2-hydroxyethyl)aminomethyl]phenol can be used to increase the heat resistance of certain fibers. Chemical Abstracts, 88, 192135j (1978) teaches that 1-phenyl-4-(3,5-di-t-butyl-4-hydroxybenzyl)piperazine is a noncolorizing thermostabilizer for stress-stable polystyrene. 2-(3,5-Di-t-butyl-4-hydroxyphenyl)ethylmethylamine is described as being useful for improving the lightfastness of dyed polyester fibers in *Chemical Abstracts*, 76, 73628q (1972).

*Chemical Abstracts*, 77, 141203v (1972) teaches that 3-(dimethylamino)propylaminobis(4-methylene-2,6-di-t-butylphenol) can be used to improve the aging resistance of diene rubber. *Chemical Abstracts*, 91 212411p (1979) describes a 1:1 pyrocatechol/4-[(dimethylamino)methyl]-2,6-di-t-butylphenol complex which deactivates transition metals in rubber. N,N-dimethyl-3,5-di-t-butyl-4-hydroxybenzylamine is disclosed to be an effective polymeriation inhibitor for styrene in *Chemical Abstracts*, 100, 35563w (1984). *Chemical Abstracts*, 107, 42468s (1987) discloses that 3-(4-hydroxy-3,5-di-t-butylphenyl)-1-aminopropane acetate or N-(4-hydroxy-3,5-di-t-butylbenzyl)-N-(β-aminoethyl)piperazine hydrochloride can be used to modify cation exchange resins so as to reduce the diffusive permeability of the resin membrane and increase its sodium ion transport properties.

Several of the phenols and benzamides of the general formula set forth above have also been found to possess various pharmacological activities. U.S. Pat. No. 3,809,761 discloses that certain of the above phenols can be used to reduce mammalian plasma lipid levels. *Chemical Abstracts*, 73, 86385w (1970) and *Chemical Abstracts*, 66, 16925d (1967) teach that certain of the above phenols have antitumor activity. *Chemical Abstracts*, 74, 96312e (1971) discloses that (4-hydroxy-3,5-di-t-butylbenzyl)methylamine hydrochloride increases the antioxidative activity of liver lipids, thereby increasing liver tissue regeneration following a partial hepatectomy. N-methyl-3,5-di-t-butyl-4-hydroxybenzylamine is said to be able to increase the rate of blood deoxygenation in *Chemical Abstracts*, 78, 132326f (1973). Finally, *Chemical Abstracts*, 109, 129047u (1988) discloses that certain benzamides of the above formula are useful for treating epilepsy and high blood pressure.

The phenols and benzamides employed in the methods of the present invention have not heretofore been used to treat inflammatory conditions, prevent ischemia-induced cell damage or treat muscular dystrophy in mammals. The known activities of such compounds, as forth above, in no way suggest the methods of the present invention. Accordingly, an object of the present invention is to provide new pharmacological uses for certain known phenols and benzamides.

Other objects, features and advantages of the present invention will become apparent from the subsequent description and the appended claims.

SUMMARY OF THE INVENTION

This invention provides a method of treating inflammation and arthritis in a mammal in need of such treatment which comprises administering to said mammal a therapeutically effective amount of a compound, or pharmaceutically acceptable salt thereof, of formula I

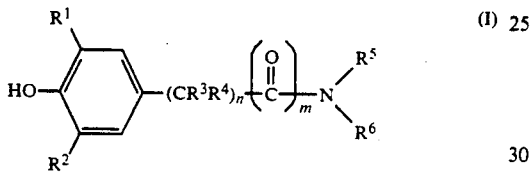

wherein:
R$^1$ and R$^2$ are each independently hydrogen, C$_1$–C$_6$ alkyl, C$_1$–C$_6$ alkoxy or

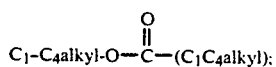

R$^3$ and R$^4$ are each independently hydrogen or C$_1$–C$_4$ alkyl;
n is an integer from 0 to 4, both inclusive;
m is 0 or 1; and
R$^5$ and R$^6$ are defined to be one of the following:

A) R$^5$ and R$^6$ are each independently hydrogen, C$_1$–C$_8$ alkyl, C$_3$–C$_8$ cycloalkyl, C$_2$–C$_8$ alkenyl, C$_2$–C$_8$ alkynyl, —(CH$_2$)$_q$ OR$^7$, —(CH$_2$)$_q$ N(R$^7$R$^8$), —(CH$_2$)$_q$ SR$^7$, —(CH$_2$)$_r$ napthyl or

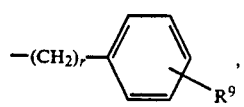

where q is an integer from 1 to 6, both inclusive, R$^7$ and R$^8$ are each independently hydrogen or C$_1$–C$_4$ alkyl, R$^9$ is hydrogen, halo, C$_1$–C$_4$ alkyl, trifluoromethyl, hydroxy, amino, C$_1$–C$_4$ alkylamino, di(C$_1$–C$_4$ alkyl)amino, phenylamino or diphenylamino, and r is an integer from 0 to 4, both inclusive;

B) one of R$^5$ or R$^6$ is as defined in (A) above and the other is

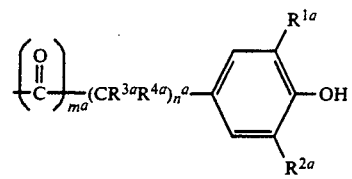

wherein m$^a$, n$^a$, R$^{1a}$, R$^{2a}$, and R$^{4a}$ are the same substituent as m, n, R$^1$, R$^2$, R$^3$ and R$^4$, respectively; or C) R$^5$ and R$^6$, taken together with the nitrogen atom to which they are attached, form

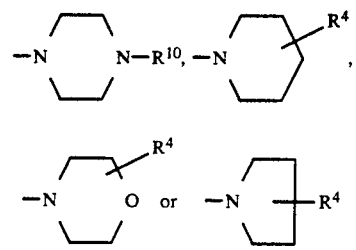

where R$^4$ is as defined above and R$^{10}$ is hydrogen, C$_1$–C$_4$ alkyl,

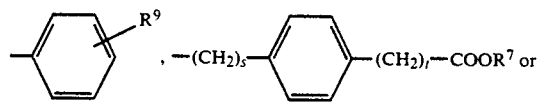

—(CH$_2$)$_t$—N(R$^7$R$^8$), where R$^7$, R$^8$, R$^9$ and r are as defined above and s and t are each independently an integer from 0 to 4, both inclusive;
with the proviso that both m and n cannot be zero.

Moreover, it has also been discovered that compounds of formula II

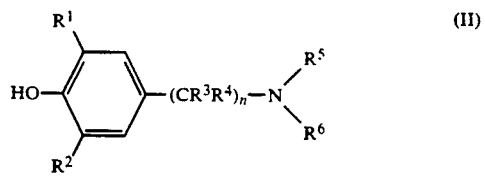

wherein:
R$^1$ and R$^2$ are each independently hydrogen, C$_1$–C$_6$ alkyl, C$_1$–C$_6$ alkoxy or

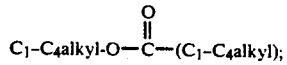

R$^3$ and R$^4$ are each independently hydrogen or C$_1$–C$_4$ alkyl;
n is an integer from 1 to 4, both inclusive; and
R$^5$ and R$^6$ are defined to be one of the following:
A) R$^5$ and R$^6$ are each independently hydrogen, C$_1$–C$_8$ alkyl, C$_3$–C$_8$ cycloalkyl, C$_2$–C$_8$ alkenyl, C$_2$–C$_8$ alkynyl, —(CH$_2$)$_q$ OR$^7$, —(CH$_2$)$_q$ N(R$^7$R$^8$), —(CH$_2$)$_q$ SR$^7$, —(CH$_2$)$_r$ napthyl or

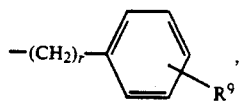

where q is an integer from 1 to 6, both inclusive, $R^7$ and $R^8$ are each independently hydrogen or $C_1$–$C_4$ alkyl, $R^9$ is hydrogen, halo, $C_1$–$C_4$ alkyl, trifluoromethyl, hydroxy, amino, di($C_1$–$C_4$alkyl-amino, di($C_1$–$C_4$ alkyl)amino, phenylamino or diphenylamino, and r is an integer from 0 to 4, both inclusive;

B) one of $R^5$ or $R^6$ is as defined in (A) above and the other is

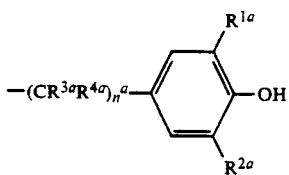

wherein $n^a$, $R^{1a}$, $R^{2a}$, and $R^{4a}$ are the same substituent as n, $R^1$, $R^2$, $R^3$ and $R^4$, respectively; or C) $R^5$ and $R^6$, taken together with the nitrogen atom to which they are attached, form

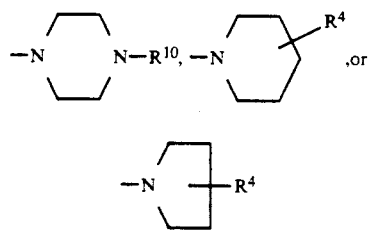

where $R^4$ is as defined above and $R^{10}$ is hydrogen, $C_1$–$C_4$ alkyl

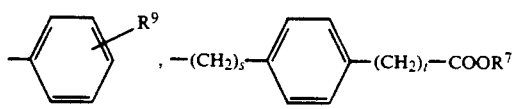

or —$(CH_2)_r$—$N(R^7R^8)$, where $R^7$, $R^8$, $R^9$ and r are as defined above and s and t are each independently an integer from 0 to 4, both inclusive; and the pharmaceutically acceptable salts thereof, are useful for preventing ischemia-induced cell damage such as may be caused by strokes, for example. This invention, therefore, also provides a method for preventing ischemia-induced cell damage in mammals by administering to a mammal in need thereof an effective ischemia reducing amount of a compound of formula II or a pharmaceutically acceptable salt thereof.

Further, it has been found that the lifespan of dystrophic mice has been prolonged by the administration of certain compounds of formula II and the pharmaceutically acceptable salts thereof. Accordingly, a method is also provided for the treatment of a dystrophic mammal by administering an effective amount of a compound of the formula II, as defined above, or a pharmaceutically acceptable salt thereof.

DETAILED DESCRIPTION OF THE INVENTION

As used herein, the term "$C_1$–$C_8$ alkyl" refers to straight and branched chain aliphatic radicals of 1 to 8 carbon atoms, both inclusive, such as methyl, ethyl, propyl, isopropyl, butyl, isobutyl, sec-butyl, tert-butyl, n-pentyl, isopentyl, n-hexyl, isohexyl, n-heptyl, n-octyl, isooctyl and the like. The term "$C_1$–$C_8$ alkyl" includes within its definition the terms "$C_1$–$C_6$ alkyl" and "$C_1$–$C_4$ alkyl".

The term "$C_1$–$C_6$ alkoxy" refers to the alkyl radicals of 1 to 6 carbon atoms, both inclusive, attached to the remainder of the molecule by oxygen and includes methoxy, ethoxy, propoxy, isopropoxy, butoxy, isobutoxy, sec-butoxy, tert-butoxy, pentoxy, hexoxy and the like.

The term "$C_2$–$C_8$ alkenyl" refers to straight and branched chain radicals of 2 to 8 carbon atoms, both inclusive, having a double bond. As such, the term includes ethylene, propylene, isopropylene, 1-butene, 2-butene, 2-methyl-1-propene, 1-pentene, 2-pentene, 2-methyl-2-butene, 1-heptene, 1-octene and the like. The term "$C_2$–$C_8$ alkenyl" includes within its definition the term "$C_2$–$C_6$ alkenyl".

The term "$C_2$–$C_8$ alkynyl" refers to straight and branched chain radicals of 2 to 8 carbon atoms, both inclusive, having a triple bond. As such, the term includes acetylene, propyne, 1-butyne, 2-butyne, 1-pentyne, 2-pentyne, 3-methyl-1-butyne, 1-hexyne, 2-hexyne, 3-hexyne, 1-heptyne, 1-octyne and the like. The term "$C_2$–$C_8$ alkynyl" includes within its definition the term "$C_2$–$C_6$ alkynyl".

The term "$C_3$–$C_8$ cycloalkyl" refers to saturated alicyclic rings of 3 to 8 carbon atoms, both inclusive, such as cyclopropyl, methylcyclopropyl, cyclobutyl, cyclopentyl, cyclohexyl, cyclooctyl and the like.

The term "naphthyl" refers to a 1-naphthyl or 2-naphthyl moiety.

The term "halo" refers to bromo, chloro, fluoro and iodo.

The pharmaceutically acceptable salts of the compounds of formulae I and II are also useful in treating arthritis, inflammation and muscular dystrophy and preventing ischemia-induced cell damage. Accordingly, such salts are included within the scope of the methods of this invention.

The term "pharmaceutically acceptable salt", as used herein, refers to salts of the compounds of formulae I and II which are substantially non-toxic to living organisms. Typical pharmaceutically acceptable salts include those salts prepared by reaction of the free base form of the compound of formulae I or II with a pharmaceutically acceptable mineral or organic acid. Pharmaceutically acceptable mineral or organic acids commonly employed to form such salts include inorganic acids such as hydrochloric, hydrobromic, hydroiodic, nitric, sulfuric and phosphoric acid, as well as organic acids such as para-toluenesulfonic, methanesulfonic, oxalic, para-bromophenylsulfonic, carbonic, succinic, citric, benzoic, acetic, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, hydrochloride, hydrobromide, hydroiodide, acetate, nitrate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-2-sulfonate, p-toluenesulfonate, mandelate and the like salts. Preferred pharmaceutically acceptable acid addition salts include those formed with mineral acids such as hydrochloric acid and nitric acid, and those formed with organic acids such as acetic acid, maleic acid, and methanesulfonic acid.

Depending upon the definitions of $R^3$, $R^4$ and n, the compounds of formulae I and II may exist in various isomeric forms. This invention is not related to any particular isomer but includes all possible individual isomers and racemates. Unless otherwise indicated, all compounds named herein are intended to exist as racemic mixtures.

The phenols and benzamides of formulae I and II are either known in the art or may be prepared by any of a number of well-known procedures. For example, many of the phenols of formulae I and II may be prepared using Mannich reaction conditions. Such conditions are well known and essentially consist of condensing ammonia or a primary or secondary amine, with an aldehyde (especially formaldehyde) and an appropriately-substituted phenol.

The phenols of formulae I and II may also be prepared using reductive amination. Such reaction entails reacting an appropriately substituted p-hydroxyphenylaldehyde (such as p-hydroxybenzaldehyde), or a ketone derivative thereof, with a primary amine so as to form an imine, which compound is then reduced with a reducing agent such as lithium aluminum hydride, sodium borohydride, sodium cyanoborohydride, hydrogen and a catalyst, or the like, to provide the corresponding amine. Reductive amination is an especially useful method for preparing the "dimer" compounds of formulae I and II, i.e., those compounds wherein one of $R^5$ or $R^6$ is

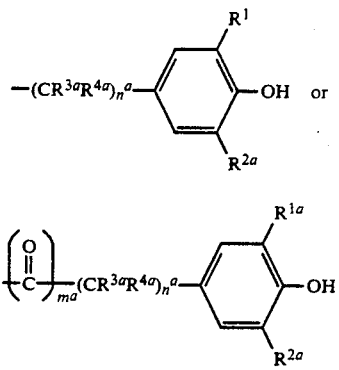

Such compounds are readily prepared by reductive amination provided the primary amine substrate is employed in a quantity sufficient to provide an amine/aldehyde or ketone mole ratio of less than about 3:1. If amine/ aldehyde or ketone mole ratios of greater than about 3:1 are employed, the "monomer" (compounds wherein neither $R^5$ nor $R^6$ are as set forth immediately above) rather than the "dimer" are preferentially obtained.

Many of the benzamides of formula I may be prepared by reacting an appropriately substituted p-hydroxyphenylcarboxylic acid, such as p-hydroxybenzoic acid or p-hydroxybenzylcarboxylic acid, or a reactive derivative thereof (such as an acid chloride), with a primary or secondary amine to form the desired benzamide. When a free carboxylic acid substrate is employed, the reaction is usually carried out in the presence of a dehydrating agent such as 1,3-dicyclohexylcarbodiimide (DCC) or N,N-carbonyldiimidazole. The benzamide thus produced may be used in the method of treating inflammation and arthritis of the present invention or, alternatively, may be converted to a phenol of formulae I and II by reduction of the amide functionality using a reducing agent such as lithium aluminum hydride, diborane or catalytic hydrogenation.

Phenols and benzamides of formulae I and II wherein $R^1$ and/or $R^2$ are $C_2$-$C_6$ alkyl may also be prepared using Friedel-Crafts alkylation conditions. Such reaction conditions are well-known and consist essentially of reacting a non-substituted or monosubstituted phenol or p-hydroxybenzamide of formulae I or II (i.e., at least one of $R^1$ and $R^2$ must be hydrogen) with a $C_2$-$C_6$ alkene in the presence of a proton acid such as sulfuric acid.

A group of preferred compounds of formulae I and II which are particularly suited for the methods of treating inflammation, arthritis and muscular dystrophy and the method of preventing ischemia-induced cell damage of the present invention are those compounds wherein $R^1$, $R^2$, $R^3$, $R^4$, m and n are as defined previously and $R^5$ and $R^6$ are defined to be one of the following:

A) $R^5$ and $R^6$ are each independently hydrogen, $C_1$-$C_6$ alkyl, $C_2$-$C_6$ alkenyl, $C_2$-$C_6$ alkynyl, —(CH$_2$)$_q$OH, —(CH$_2$)$_q$NH$_2$, —(CH$_2$)$_q$NH(C$_1$-C$_4$ alkyl), —(CH$_2$)$_q$N(C$_1$-C$_4$ alkyl)$_2$, —(CH$_2$($_q$S(C$_1$-C$_4$ alkyl) or

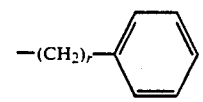

where q and r are both as previously defined;

B) one of $R^5$ and $R^6$ is as defined in (A) immediately above and the other is

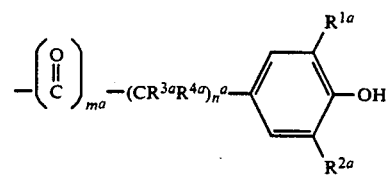

(for formula I) or

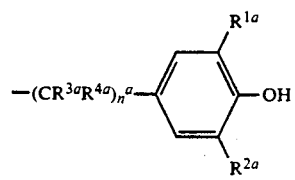

(for formula II) wherein $m^a$, $n^a$, $R^{1a}$, $R^{2a}$, $R^{3a}$, and $R^{4a}$, and $n^a$, $R^{1a}$, $R^{2a}$, $R^{3a}$, and $R^{4a}$ are the same substituent as m, n, $R^1$, $R^2$, $R^3$, and $R^4$ and n, $R^1$, $R^2$, $R^3$ and $R^4$, respectively; or C) $R^5$ and $R^6$, taken together with the nitrogen atom to which they are attached, form

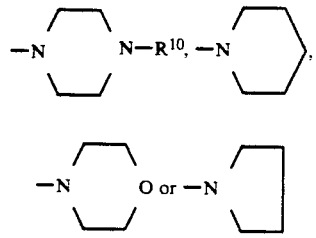

(for formula I) or

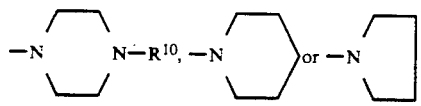

(for formula II) wherein $R^{10}$ is hydrogen or $C_1-C_4$ alkyl.

In this preferred group of compounds, the following substituents are especially preferred.

i) $R^1$ and $R^2$ are each independently $C_1-C_4$ alkyl;
ii) one of $R^1$ and $R^2$ is 1,1-dimethylethyl and the other is $C_1-C_4$ alkyl;
iii) one of $R^1$ and $R^2$ is 1,1-dimethylethyl and the other is methyl;
iv) $R^1$ and $R^2$ are both 1,1-dimethylethyl;
v) one of $R^1$ and $R^2$ is 1,1-dimethylethyl and the other is hydrogen;
vi) one of $R^3$ and $R^4$ is hydrogen and the other is hydrogen or $C_1-C_4$ alkyl;
vii) one of $R^3$ and $R^4$ is hydrogen and the other is methyl;
viii) $R^3$ and $R^4$ are both hydrogen;
ix) n is 0 and m is 1;
x) n is 1 and m is 0;
xi) n is 2 and m is 0;
xii) $R^5$ and $R^6$ are each independently hydrogen or $C_1-C_6$ alkyl;
xiii) $R^5$ and $R^6$ are each independently hydrogen or $C_1-C_4$ alkyl;
xiv) $R^5$ and $R^6$ are each independently hydrogen or methyl;
xv) $R^5$ and $R^6$ are each independently hydrogen or ethyl;
xvi) $R^5$ and $R^6$ are each independently hydrogen or n-propyl;
xvii) $R^5$ and $R^6$ are each independently hydrogen or n-butyl;
xviii) $R^5$ and $R^6$ are each independently hydrogen or t-butyl;
xix) $R^5$ and $R^6$ are both methyl;
xx) $R^5$ and $R^6$ are both ethyl;
xxi) $R^5$ and $R^6$ are both n-propyl;
xxii) $R^5$ and $R^6$, taken together with the nitrogen atom to which they are attached, form

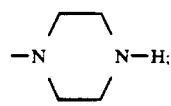

xxiii) $R^5$ and $R^6$, taken together with the nitrogen atom to which they are attached, form

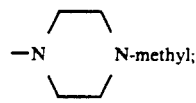

xxiv) $R^5$ and $R^6$, taken together with the nitrogen atom to which they are attached, form

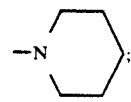

xxv) $R^5$ and $R^6$, taken together with the nitrogen atom to which they are attached, form

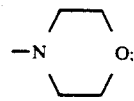

xxvi) $R^5$ and $R^6$, taken together with the nitrogen atom to which they are attached, form

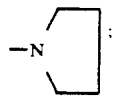

xxvii) pharmaceutically acceptable salts of any of the above compounds.

Especially preferred compounds which can be used in the methods of the present invention are compounds of the formula

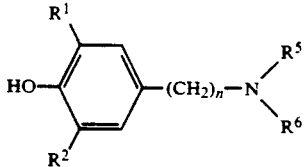

wherein $R^1$ and $R^2$ are either both 1,1-dimethylethyl or one of $R^1$ and $R^2$ is hydrogen or methyl and the other is 1,1-dimethylethyl, n is an integer from 1 to 4, both inclusive, and $R^5$ and $R^6$ are each independently hydrogen or $C_1-C_4$ alkyl or, when taken together with the nitrogen atom to which they are attached, form

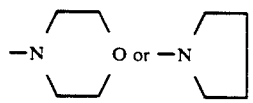

(for formula I) or

(for formula II).

The most preferred compounds which may be used in the method of treating inflammation and arthritis of the present invention include 4-[(dimethylamino)methyl]-2,6-bis(1,1-dimethylethyl)phenol, 4-(4-morpholinylmethyl)-2,6-bis(1,1-dimethylethyl)phenol, 4-[2-(methylamino)ethyl]-2,6-bis(1,1-dimethylethyl)phenol, 4-[(methylamino)methyl]-2,6-bis(1,1-dimethylethyl)phenol, 4-[(ethylamino)methyl]-2,6-bis(1,1-dimethylethyl)phenol, 4-[2-(methylamino)ethyl]-2-(1,1-dimethylethyl)phenol and the pharmaceutically acceptable salts thereof.

The most preferred compounds which may be used in the method of preventing ischemia-induced cell damage of the present invention include 4-[(dimethylamino)methyl]-2,6-bis(1,1-dimethylethyl)phenol, 4-2-(dimethylamino)ethyl]-2,6-bis(1,1-dimethylethyl)phenol, 4-(N-ethyl-N-methylamino)methyl]-2,6-bis(1,1-dimethylethyl)phenol, 4-(methylamino)methyl]-2,6-bis(1,1-dimethylethyl)phenol, 4-[(ethylamino)methyl]-2,6-bis(1,1-dimethylethyl)phenol, 4-{[(1,1-dimethylethyl)amino]methyl}-2,6-bis(1,1-dimethylethyl)phenol, 4-[(n-propylamino)methyl]-2,6-bis(1,1-dimethylethyl)phenol and the pharmaceutically acceptable salts thereof.

The most preferred compounds which may be used in the method of treating muscular dystrophy encompassed within the present invention are 4-[(dimethylamino)methyl]-2,6-bis(1,1-dimethylethyl)phenol, 4-[(ethylamino)methyl]-2,6-bis(1,1-dimethylethyl)phenol and the pharmaceutically acceptable salts thereof.

Typical examples of compounds of formulae I and II which are useful in treating inflammation, arthritis and muscular dystrophy and preventing ischemia-induced cell damage according to this invention include:

4-[(dimethylamino)methyl]-2,6-bis(1,1-dimethylethyl)phenol
4-[(dimethylamino)methyl]-2,6-bis(1,1-dimethylethyl)phenol hydrochloride
4-[(dimethylamino)methyl]-2,6-bis(1,1-dimethylethyl)phenol methanesulfonate
N,N-dimethyl-3,5-bis(1,1-dimethylethyl)-4-hydroxybenzamide
4-{[N-methyl-N-(4-hydroxy-3,5-bis(1,1-dimethylethyl)benzyl)amino]methyl}-2,6-bis(1,1-dimethylethyl)phenol
4-{[N-methyl-N-(4-hydroxy-3,5-bis(1,1-dimethylethyl)benzyl)amino]methyl}-2,6-bis(1,1-dimethylethyl)phenol hydrochloride
4-[2-(dimethylamino)ethyl]-2,6-bis(1,1-dimethylethyl)phenol
4-[2-(dimethylamino)ethyl]-2,6-bis(1,1-dimethylethyl)phenol hydrochloride
4-[2-(methylamino)ethyl]-2,6-bis(1,1-dimethylethyl)phenol hydrochloride
4-(4-morpholinylmethyl)-2,6-bis(1,1-dimethylethyl)phenol
4-(4-morpholinylmethyl)-2,6-bis(1,1-dimethylethyl)phenol hydrochloride
4-(1-pyrrolidinomethyl)-2,6-bis(1,1-dimethylethyl)phenol
4-(1-pyrrolidinomethyl)-2,6-bis(1,1-dimethylethyl)phenol hydrochloride
4-[(N-ethyl-N-methylamino)methyl]-2,6-bis(1,1-dimethylethyl)phenol methanesulfonate
4-[(diethylamino)methyl]-2,6-bis(1,1-dimethylethyl)phenol hydrochloride
4-[(dipropylamino)methyl]-2,6-bis(1,1-dimethylethyl)phenol hydrochloride
4-[(methylamino)methyl]-2,6-bis(1,1-dimethylethyl)phenol hydrochloride
4-[(ethylamino)methyl]-2,6-bis(1,1-dimethylethyl)phenol hydrochloride
4-[(ethylamino)methyl]-2,6-bis(1,1-dimethylethyl)phenol nitrate
4-{[(1,1-dimethylethyl)amino]methyl}-2,6-bis(1,1-dimethylethyl)phenol hydrochloride
4-[2-(methylamino)ethyl]-2-(1,1-dimethylethyl)phenol hydrochloride
4-[(dimethylamino)methyl]-2-(1,1-dimethylethyl)-6-methyl phenol
4-[(n-propylamino)methyl]-2,6-bis(1,1-dimethylethyl)phenol hydrochloride
4-[1-(ethylamino)ethyl]-2,6-bis(1,1-dimethylethyl)phenol hydrochloride
4-[(dipropylamino)methyl]-2,6-bis(1,1-dimethylethyl)phenol
4-[(N-ethyl-N-methylamino)methyl]-2,6-bis(1,1-dimethylethyl)phenol
4-[(diethylamino)methyl]-2,6-bis(1,1-dimethylethyl)phenol
4-[(n-propylamino)methyl]-2-ethylphenol
4-[(dimethylamino)methyl]-2,6-dimethylphenol
4-[(N-n-butyl-N-cyclohexylamino)methyl]-2,6-bis(1,1-dimethylethyl)phenol acetate
4-[3-(dicycloheptylamino)propyl]-2,6-diethoxyphenol
4-[2-(diphenylamino)ethyl]-2,6-diethylphenol tartrate
4-{4-N-hexyl-N-(3-butene)amino]butyl}-2-methoxyphenol
4-{[(2-(dimethylamino)ethyl)amino]methyl}-2,6-diisopropylphenol hydrobromide
4-{[N-ethyl-N-(3-phenylpropyl)amino]methyl}-2-ethyl-6-methylphenol
4-{2-[N-cyclopentyl-N-(aminomethyl)amino]ethyl]-2-(1,1-dimethylethyloxy)phenol
4-{2-[(2-hydroxyethyl)amino]ethyl}-2-propylphenol citrate
4-(1-piperidinylmethyl)-2,6-diethylphenol
4-(1-piperidinylmethyl)-2,6-diethylphenol hydrobromide
4-[1-(3-ethyl)piperidinylmethyl]-2,6-dimethoxyphenol
4-[4-(2-methyl)morpholinylmethyl]-2-(1,1-dimethylethyl)phenol phosphate
4-[2-(piperazinyl)ethyl]-2-n-butyl-6-methylphenol
4-{3-[1-(4-methyl)piperazinyl]propyl}-2-ethoxy-6-isopropylphenol toluenesulfonate
N-isopropyl-N-cyclobutyl-3,5-dimethyl-4-hydroxybenzamide hydrochloride
N-(methylthiomethyl)-3-(1,1-dimethylethyl)-4-hydroxybenzamide decanoate
N,N-diethylene-3-ethoxy-4-hydroxy-5-isopropylbenzamide maleate
(−)-4-[1-(methylamino)ethyl]-2,6-diethylphenol
(+)-4-[1-(diethylamino)butyl-2-methoxyphenol lactate
(+)-4-[1-methyl-2-(cyclohexylamino)butyl]-2-isopropyl-6-methylphenol sulfate (-)-4-{1-[1-(4-n-propyl)piperazinyl]ethyl}-2-ethoxy-6-methoxyphenol hydroxybenzoate (-)-4-[1-(2-phenylethylamino)propyl]-2,6-bis(1,1-dimethylethyl)phenol sulfite N,N-diethyl-[3-(3,5-diethyl-4-hydroxyphenyl)propyl]carboxamide N-octyl-[(3-isopropyl-4-hydroxyphenyl)methyl]carboxamide heptanoate N-methyl-N-n-propyl-[2-(3,5-diisobutoxy-4-hydroxyphenyl)ethyl]carboxamide formate N-2-chlorophenyl-3,5-bis(1,1-dimethylethyl)-4-hydroxybenzamide 4-[(isopropylamino)methyl]-2,6-bis(1,1-dimethylethyl)phenol 4-[(isopropylamino)methyl]-2,6-bis(1,1-dimethylethyl)phenol hydrochloride As noted previously, the compounds of formula I are useful for treating inflammation and arthritis and the compounds of formula II are useful for treating muscular dystrophy and preventing ischemia-induced cell damage. Such activities were demonstrated in the following test systems.

DEVELOPING ADJUVANT-INDUCED ARTHRITIS TEST IN RATS

Compounds were tested for their ability to alter hind paw swelling and bone damage resulting from adjuvant-induced edema in rats. In order to quantitate the inhibition of hind paw swelling resulting from adjuvant-induced arthritis, two phases of inflammation have been defined: (1) the primary and secondary injected hind paw, and (2) the secondary uninjected hind paw, which generally begins developing about eleven days from the induction of inflammation in the injected paw. Reduction of the latter type of inflammation is an indication of immunosuppressive activity. Cf. Chang, *Arth. Rheum.*, 20, 1135-1141 (1977).

Adjuvant arthritis was induced in male Lewis-Wistar rats (200-210 grams) by a single subplantar injection into the right hind paw of 0.1 ml of a 0.5% suspension of heat-killed, lyophilized *Mycobacterium tuberculosis* (Calbiochem-Perrigen-C) in mineral oil (a modification of a method reported by Winter et al., *Arth. Rheum.*, 9, 394-397 (1966)). One group of 10 rats ("TB control") received only this treatment. Another group of 5 rats received no treatment (normal control). Each compound to be tested was suspended in carboxymethylcellulose (1%) and administered once per day p.o. to rats (groups of 5 each) beginning on day one and continuing through the 28th day after the adjuvant injection (29 doses total). Paw volumes were measured by mercury displacement using a Statham pressure transducer and digital voltmeter. Volumes of both the injected and the uninjected hind paws were measured on days 16, 18, 21, 23, 25, 28, and 30. X-ray photos were taken on day 30, after the animals were sacrificed. The paw volume measurements on the uninjected paw beginning with day 16 through day 30 were computer plotted for the TB controls, the normal controls, and the drug-treated animals, and the areas under the curves [(TB controls minus normal controls) and (treated animals minus normal controls)] were determined. The results are summarized in Table I.

TABLE I

Inhibition of Uninjected Paw Volume Inflammation Days 16-30

| Antiinflammatory Agent | Dose mg/kg rat weight × 29 | % Inhibition* |
|---|---|---|
| 4-[(dimethylamino)methyl]-2,6-bis(1,1-dimethylethyl)phenol hydrochloride | 50 | 94.8 |
| 4-[(N-ethyl-N-methylamino)methyl]-2,6-bis(1,1-dimethylethyl)phenol methanesulfonate | 25 | 26.0 |
| 4-(4-morpholinylmethyl)-2,6-bis(1,1-dimethylethyl)phenol | 50 | 71.1 |
| 4-(4-morpholinylmethyl(-2,6-bis(1,1-dimethylethyl)phenol | 25 | 40.6 |
| 4-[(dipropylamino)methyl]-2,6-bis(1,1-dimethylethyl)phenol hydrochloride | 50 | 64.4 |
| 4-{[N-methyl-N-(4-hydroxy-3,5-bis(1,1-dimethylethyl)benzyl)-amino]methyl}-2,6-bis(1,1-dimethylethyl)phenol | 50 | 77.0 |
| 4-[(methylamino)methyl]-2,6-bis-(1,1-dimethylethyl)phenol hydrochloride | 50 | 119.1 |
| 4-[(ethylamino)methyl]-2,6-bis-(1,1-dimethylethyl)phenol hydrochloride | 25 | 96.5 |
| 4-[(ethylamino)methyl]-2,6-bis-(1,1-dimethylethyl)phenol hydrochloride | 20 | 50.8 |
| 4-[(ethylamino)methyl]-2,6-bis(1,1-dimethylethyl)phenol hydrochloride | 10 | 19.6 |
| 4-[(ethylamino)methyl]-2,6-bis(1,1-dimethylethyl)phenol hydrochloride | 5 | 27.9 |
| 4-[(isopropylamino)methyl]-2,6-bis(1,1-dimethylethyl)phenol hydrochloride | 25 | 4.9 |
| 4-[2-(methylamino)ethyl]-2-(1,1-dimethylethyl)phenol hydrochloride | 25 | 76.6 |
| 4-[2-(methylamino)ethyl]-2,6-bis(1,1-dimethylethyl)phenol hydrochloride | 25 | 72.2 |
| 4-{[1,1-(dimethylethyl)amino]-methyl}-2,6-bis(1,1-dimethylethyl)phenol hydrochloride | 25 | 3.9 |
| 4-[(dimethylamino)methyl]-2,6-bis(1,1-dimethylethyl)phenol | 50 | 59.7 |
| N-2-chlorophenyl-3,5-bis(1,1-dimethylethyl)-4-hydroxybenzamide | 50 | 8.7 |
| N,N-dimethyl-3,5-bis(1,1-dimethylethyl)-4-hydroxybenzamide | 50 | 64.4 |

*% inhibition is the difference of the areas under the curves (AUC) of the mean uninjected paw volumes plotted for days 16, 18, 21, 23, 25, 28 and 30 according to the following formula:

% inhibition = $\left[1 - \frac{(\text{Drug treated AUC}) - (\text{normal control AUC})}{(\text{TB control AUC}) - (\text{normal control AUC})}\right] \times 100$

STROKE MODEL IN RATS

Strokes were produced in rats by occluding the four arteries that supply blood to the brain according to the following procedure. Male Wistar rats (250-280 g; Hilltop Laboratories, Scottsdale, Pa.) were anesthetized with metofane and placed into a stereotaxic instrument. A longitudinal incision was made on the dorsal surface of the neck. The neck muscles were reflected to expose the dorsal surface of the spinal column. The two vertebral arteries were exposed where they pass through the first cervical vertebra. Both arteries were permanently occluded by the application of electrocautery. After coagulation of the vertebral arteries, the rat was removed from the stereotaxic instrument and the surgical wound was sutured. Two longitudinal incisions were then made on the ventral surface of the neck. The two common carotid arteries were exposed and dissected free from surrounding nerves and connective tissue. Reversible atraumatic clamps, fabricated mainly from silicon rubber tubing, were placed around each carotid artery in a manner such that the vessels were not traumatized or occluded. The clamps were externalized through the ventral neck incision. A suture was also placed through the neck dorsal to the carotids, esophagus and trachea, and tied loosely behind the neck. This suture is tied tightly at the time ischemia is induced in order to restrict collateral circulation reaching the brain through the dorsal muscles of the neck. The surgical wounds were then closed. After the surgery, the rats were allowed to recover for 24 hours (free access to water, but no food during this period).

On the day of testing, test compounds were administered at various times before stroke induction. Strokes (cerebral ischemia) were induced by tightening the clamps around the carotids, thereby stopping blood flow in the carotids. Rats in which strokes were successfully produced lost the righting reflex and became unresponsive to stimuli. Collateral circulation through the dorsal neck muscles was then restricted by tightening the previously implanted suture. Rats which did not become unconscious at this time were discarded. After 30 minutes of ischemia, the carotid clamps were released, the neck suture was loosened, and blood flow to the brain was restored. Following the period of ischemia, the rats were allowed free access to food and water. Rats were again treated with test compounds at various times after the stroke. On the third day after the stroke the animals were sacrificed and their brains were removed, frozen and sectioned through the striatum and hippocampus. Sections were mounted on glass slides and stained with hematoxylin and eosin.

Two of the areas of the brain that are most susceptible to ischemia induced damage, both in rats and humans, are the $CA_1$ pyramidal cell layer of the hippocampus and the striatal cell layer of the striatum. In animals that remain unresponsive for the 30 minute period of ischemia, the $CA_1$ pyramidal cell layer and the striatal cell layer are completely destroyed. These layers of cells were examined microscopically in histological sections prepared from the hippocampus and striatum. Brain damage was rated according to the following scale:

0 = no damage, completely intact cell layer
1 = mild damage, one-third of cell layer dead
2 = moderate damage, two-thirds of cell layer dead
3 = severe damage, complete destruction of cell layer Damage in 10-12 sections from each brain was assessed in order to obtain an accurate estimate of damage. An average damage score was calculated for each treatment group. Scores from treated groups were compared statistically with scores from control groups which received only the vehicle used to suspend the compounds. The level of significance was determined using the Mann Whitney-U-test. Results are summarized in Table II.

TABLE II

Prevention of ischemia-induced cell damage in the hippocampal $CA_1$ and striatal region in rats

| Compound/Control | Vehicle | Dose* | Method of Admin. | Time of** Admin. | No. of Rats | Damage Score*** Hippocampus | Striatum |
|---|---|---|---|---|---|---|---|
| Control | 2% acacia | — | orally | a | 12 | 2.7 ± 0.2 | 2.6 ± 0.2 |
| 4-[(dimethylamino)methyl]-2,6-bis(1,1-dimethylethyl)phenol hydrochloride | 2% acacia | 50 | orally | a | 16 | 1.7 ± 0.3 | 1.1 ± 0.2 |
| Control | 2% acacia | — | orally | b | 6 | 2.8 ± 0.2 | 2.5 ± 0.5 |
| 4-[(dimethylamino)methyl]-2,6-bis(1,1-dimethylethyl)phenol | 2% acacia | 100 | orally | b | 12 | 0.8 ± 0.4 | 0.8 ± 0.3 |
| Control | 2% acacia | — | orally | a | 9 | 2.9 ± 0 0.1 | 2.4 ± 0.4 |
| 4-[(dimethylamino)methyl]-2,6-bis(1,1-dimethylethyl)phenol methanesulfonate | 2% acacia | 100 | orally | a | 11 | 0.9 ± 0.3 | 0.8 ± 0.3 |
| Control | 2% acacia | — | orally | c | 13 | 2.7 ± 0.2 | 2.7 ± 0.2 |
| 4-{[N-methyl-N-(4-hydroxy-3,5-bis(1,1-dimethylethyl)benzyl)-amino]methyl}-2,6-bis-(1,1-dimethylethyl)-phenol hydrochloride | 2% acacia | 100 | orally | c | 12 | 2.9 ± 0.1 | 1.8 ± 0.4 |
| 4-[2-(dimethylamino)-ethyl]-2,6-bis(1,1-dimethylethyl)phenol hydrochloride | 2% acacia | 100 | orally | c | 8 | 0.2 ± 0.2 | 0.0 ± 0.0 |
| 4-{[N-methyl-N-(4-hydroxy-3,5-bis(1,1-dimethylethyl)benzyl)-amino]methyl}-2,6-bis-(1,1-dimethylethyl)phenol | 2% acacia | 100 | orally | c | 9 | 2.9 ± 0.2 | 2.4 ± 0.4 |
| 4-[2-(dimethylamino)-ethyl]-2,6-bis(1,1-dimethylethyl)phenol | 2% acacia | 100 | orally | c | 12 | 0.0 ± 0.0 | 0.0 ± 0.0 |
| Control | water | — | orally | a | 13 | 2.7 ± 0.2 | 2.7 ± 0.2 |
| 4-[2-(dimethylamino)-ethyl]-2,6-bis(1,1-dimethylethyl)phenol hydrochloride | water | 100 | orally | a | 8 | 0.2 ± 0.2 | 0.1 ± 0.0 |

TABLE II-continued

Prevention of ischemia-induced cell damage in the hippocampal CA$_1$ and striatal region in rats

| Compound/Control | Treatment Vehicle | Dose* | Method of Admin. | Time of** Admin. | No. of Rats | Damage Score*** Hippocampus | Striatum |
|---|---|---|---|---|---|---|---|
| Control | water | — | orally | a | 8 | 3.0 ± 0.0 | 2.8 ± 0.2 |
| 4-[2-(dimethylamino)-ethyl]-2,6-bis(1,1-dimethylethyl)phenol hydrochloride | water | 50 | orally | a | 10 | 0.8 ± 0.4 | 0.3 ± 0.2 |
| Control | water | — | orally | a | 10 | 2.5 ± 0.3 | 2.5 ± 0.3 |
| 4-[2-(dimethylamino)-ethyl]-2,6-bis(1,1-dimethylethyl)phenol hydrochloride | water | 25 | orally | a | 12 | 1.6 ± 0.3 | 0.9 ± 0.3 |
| Control | 2% acacia | — | orally | c | 10 | 2.90 ± 0.04 | 2.30 ± 0.32 |
| 4-[2-(methylamino)-ethyl]-2,6-bis(1,1-dimethylethyl)phenol hydrochloride | 2% acacia | 50 | orally | c | 10 | 2.04 ± 0.32 | 1.35 ± 0.34 |
| Control | 2% acacia | — | orally | c | 9 | 2.5 ± 0.3 | 1.4 ± 0.3 |
| 4-(1-pyrrolidinomethyl)-2,6-bis(1,1-dimethyl-ethyl)phenol hydrochloride | 2% acacia | 100 | orally | c | 8 | 1.2 ± 0.5 | 1.5 ± 0.4 |
| Control | 2% acacia | — | orally | a | 9 | 2.9 ± 0.1 | 2.4 ± 0.4 |
| 4-[N-ethyl-N-methyl-amino)methyl]-2,6-bis-(1,1-dimethylethyl)-phenol methanesulfonate | 2% acacia | 100 | orally | a | 8 | 1.1 ± 0.5 | 1.1 ± 0.4 |
| Control | 2% acacia | — | orally | c | 9 | 2.5 ± 0.3 | 1.4 ± 0.3 |
| 4-[(diethylamino)-methyl]-2,6-bis(1,1-dimethylethyl)phenol hydrochloride | 2% acacia | 100 | orally | c | 6 | 2.0 ± 0.5 | 1.7 ± 0.6 |
| 4-[(dipropylamino)-methyl]-2,6-bis(1,1-dimethylethyl)phenol hydrochloride | 2% acacia | 100 | orally | c | 9 | 1.0 ± 0.4 | 1.2 ± 0.4 |
| Control | saline sol. | —/— | i.v. | d | 9 | 2.6 ± 0.3 | 2.3 ± 0.4 |
| 4-[(methylamino)-methyl]-2,6-bis(1,1-dimethylethyl)phenol hydrochloride | saline sol. | 50/10 | i.v. | d | 11 | 0.66 ± 0.3 | 1.13 ± 0.4 |
| Control | saline sol. | —/— | i.v. | d | 10 | 2.4 ± 0.3 | 2.6 ± 0.3 |
| 4-[(methylamino)-methyl]-2,6-bis(1,1-dimethylethyl)phenol hydrochloride | saline sol. | 10/10 | i.v. | d | 8 | 0.75 ± 0.3 | 1.97 ± 0.4 |
| Control | 2% acacia | — | orally | c | 12 | 2.95 ± 0.03 | 2.93 ± 0.05 |
| 4-[(ethylamino)-methyl]-2,6-bis(1,1-dimethylethyl)phenol hydrochloride | 2% acacia | 50 | orally | c | 11 | 0.66 ± 0.29 | 0.72 ± 0.27 |
| Control | 10% DMSO/ TWEEN 80/ NaCl sol. | —/— | i.v. | d | 9 | 2.83 ± 0.12 | 2.37 ± 0.28 |
| 4-[(ethylamino)-methyl]-2,6-bis(1,1-dimethylethyl)phenol hydrochloride | 10% DMSO/ TWEEN 80/ NaCl sol. | 20/5 | i.v. | d | 10 | 1.23 ± 0.47 | 1.20 ± 0.42 |
| Control | 2% acacia | — | orally | c | 10 | 2.90 ± 0.04 | 2.30 ± 0.32 |
| 4-[(ethylamino)-methyl]-2,6-bis-(1,1-dimethylethyl)phenol nitrate | 2% acacia | 50 | orally | c | 9 | 1.81 ± 0.36 | 1.26 ± 0.40 |
| Control | 2% acacia | — | orally | c | 9 | 2.73 ± 0.22 | 2.71 ± 0.22 |
| 4-{[(1,1-dimethyl-ethyl)amino]methyl}-2,6-bis(1,1-dimethyl-ethyl)phenol hydro-chloride | 2% acacia | 50 | orally | c | 9 | 1.72 ± 0.43 | 0.75 ± 0.35 |
| 4-[2-(methylamino)-ethyl]-2-(1,1-dimethyl-ethyl)phenol hydro-chloride | 2% acacia | 50 | orally | c | 10 | 2.78 ± 0.12 | 1.62 ± 0.35 |
| Control | distilled water | — | orally | c | 13 | 2.96 ± 0.03 | 2.53 ± 0.22 |
| 4-[(n-propylamino)-methyl]-2,6-bis(1,1-dimethylethyl)phenol hydrochloride | distilled water | 50 | orally | c | 13 | 1.48 ± 0.34 | 1.05 ± 0.33 |

TABLE II-continued

Prevention of ischemia-induced cell damage in the hippocampal $CA_1$ and striatal region in rats

| Compound/Control | Treatment | | | | No. of Rats | Damage Score*** | |
| --- | --- | --- | --- | --- | --- | --- | --- |
| | Vehicle | Dose* | Method of Admin. | Time of** Admin. | | Hippocampus | Striatum |
| Control | 2% acacia | — | orally | c | 12 | 2.6 ± 0.3 | 1.9 ± 0.4 |
| 4-[1-(ethylamino)-ethyl]-2,6-bis(1,1-dimethylethyl)phenol hydrochloride | 2% acacia | 50 | orally | c | 7**** | 0.9 ± 0.4 | 1.5 ± 0.5 |
| 4-[1-(ethylamino)-ethyl]-2,6-bis(1,1-dimethylethyl)phenol hydrochloride | saline sol. | 20/5 | i.v. | d | — | test abandoned because of toxicity problems | |

*compound - mg/kg rat weight (orally) or mg/kg rat weight/mg/kg rat weight per hour (i.v.); compound administered as a suspension in vehicle (orally) or dissolved in vehicle (i.v.)
control - same volume of vehicle administered as the volume (active ingredient plus vehicle) administered to test animal;
**times of administration are as follows:
a - dose administered 15 minutes prior to ischemia, 4 hours post-ischemia and 24 hours post-ischemia;
b - dose administered 2 hours prior to ischemia and 24 hours post-ischemia;
c - dose administered 30 minutes prior to ischemia, 4 hours post-ischemia and 24 hours post-ischemia;
d - initial dose administered immediately after ischemia followed by continuous administration for the next 24 hours.
***mean ± standard error
****data obtained on only 7 rats because of toxicity problems Compounds of formula II have been shown to prevent ischemia-induced cell damage in mammals. Accordingly, such compounds are useful for the treatment of cell damage caused by ischemic vascular disorders such as cardiac infarction, angina pectoris, cerebral infarction, cerebral hemorrhage, kidney infarction, pulmonary infarction, intermittent claudication, transient cerebral attack, subarachinoid hemorrhage, thrombosis or ischemic damage resulting from head or central nervous system trauma. A preferred ischemic vascular disorder against which the compounds of formula II are particularly effective is ischemia-induced cell damage caused by stroke. Such activity was demonstrated in the following test system.

MIDDLE CEREBRAL ARTERY OCCLUSION STROKE MODEL

Strokes were also produced in rats by occluding the middle cerebral artery according to the following procedure. Male spontaneously hypertensive rats were housed in groups of three to four per cage and allowed free access to food and water. The animals were anesthetized with a mixture of 2.5% halothane and air. The anesthetized rats then underwent the following surgical procedure.

A femoral artery of each rat was cannulated to monitor mean arterial pressure and a jugular cannula was inserted in order to provide a means for administering test compounds intravenously. Focal ischemia of the right neocortex was produced by occluding first the right common carotid artery and then the right middle cerebral artery just superior to the rhinal fissure. The ventral neck area and the area behind each animal's right eye were shaved and washed with antiseptic solution. The right common carotid artery was dissected free of connective tissue through a midline cervical incision and the vessel permanently occluded with a silk ligature. Next, a 1 cm incision perpendicular to, and bisecting a line between the lateral canthus of the right eye and the external auditory canal, was made to expose the temporalis muscle which was retracted and partially excised. Using a dissecting microscope, the right middle cerebral artery was exposed through a 2 mm burr hole drilled 2-3 mm rostral to the fusion of the zygomatic arch with a squamosal bone. Drilling was done under a continuous drip of a 0.9% saline solution to prevent heat injury of the underlying cortex. The dura was cut and retracted to expose the middle cerebral artery.

This artery was occluded in two ways. The first method of occlusion involved permanent cauterization of the artery so that blood flow through the artery was completely eliminated. The second method of occlusion was only temporary (lasting two hours) and involved clamping the artery with microaneurism clips. Test compounds were administered at various times before, during and after occlusion. Each animal's body temperature was maintained at 37° C. during testing using a rectal thermometer connected to a heating pad.

Twenty-four hours after tandem middle cerbral carotid artery occlusion, the test animals were sacrificed and their brains removed and frozen over dry ice. Coronal sections 20 microns thick were cut at half millimeter intervals in a cryostat at −20° C. and dried on a hot plate at 60° C. The sections were then stained with cresyl violet. Infarcted brain did not take up the stain and was readily detected and digitized while projected on a digitizing tablet, thereby allowing measurement of the infarcted area of each section. A total infarct volume was then calculated using a computer program that summed all sectional areas measured multiplied by the interval thickness. The lower the infarcted volume obtained, the lower the amount of cell damage caused by the stroke. The level of significance was obtained using Student's "t-test". Results are summarized in Table III.

TABLE III

Prevention of Ischemia-Induced Cell Damage Caused by Middle Cerebral Artery Occlusion

| Compound/Control | Method of Occlusion | Vehicle | Dose* | Method of Admin. | Time of Admin.** | No. of Rats | Infarct Volume (mm)³ |
| --- | --- | --- | --- | --- | --- | --- | --- |
| Control | temporary | saline sol. | —/—/— | i.p./i.p./i.v. | a | 8 | 114.4 ± 14.1 |
| 4-[(dimethylamino)methyl]-2,6-bis(1,1-dimethylethyl) | temporary | saline sol. | 50/50/10 | i.p./i.p./i.v. | a | 7 | 47.9 ± 3.4 |

TABLE III-continued

Prevention of Ischemia-Induced Cell Damage Caused by Middle Cerebral Artery Occlusion

| Compound/Control | Method of Occlusion | Vehicle | Dose* | Method of Admin. | Time of Admin.** | No. of Rats | Infarct Volume (mm)³ |
|---|---|---|---|---|---|---|---|
| phenol hydrochloride | | | | | | | |
| Control | temporary | saline sol. | —/—/— | i.p./i.p./i.v. | b | 4 | 101.7 ± 9.1 |
| 4-[(dimethylamino)methyl]-2,6-bis(1,1-dimethylethyl)phenol hydrochloride | temporary | saline sol. | 50/50/10 | i.p./i.p./i.v. | b | 4 | 35.5 ± 5.3 |
| Control | permanent | saline sol. | —/— | i.v. | c | 15 | 136 ± 7 |
| 4-[(dimethylamino)methyl]-2,6-bis(1,1-dimethylethyl)phenol hydrochloride | permanent | saline sol. | 50/10 | i.v. | c | 11 | 91 ± 12 |
| Control | temporary | saline sol. | —/—/— | i.p./i.p./i.v. | b | 10+ | 61.9 ± 7.9 |
| 4-[(dimethylamino)methyl]-2,6-bis(1,1-dimethylethyl)phenol hydrochloride | temporary | saline sol. | 50/50/10 | i.p./i.p./i.v. | b | 7+ | 23.1 ± 4.9 |
| Control | temporary | saline sol. | —/— | i.v. | d | 14 | 97 ± 10 |
| 4-[(dimethylamino)methyl]-2,6-bis(1,1-dimethylethyl)phenol methanesulfonate | temporary | saline sol. | 30/5 | i.v. | d | 15 | 69 ± 9 |
| Control | temporary | saline sol. | —/— | i.v. | d | 7 | 84.7 ± 6.4 |
| 4-[2-(dimethylamino)ethyl]-2,6-bis(1,1-dimethylethyl)phenol hydrochloride | temporary | saline sol. | 20/5 | i.v. | d | 7 | 77.6 ± 5.5 |
| Control | permanent | saline sol. | —/— | i.v. | c | 10 | 154 ± 11 |
| 4-[2-(dimethylamino)ethyl]-2,6-bis(1,1-dimethylethyl)phenol hydrochloride | permanent | saline sol. | 10/5-++ | i.v. | c | 9 | 161 ± 17 |
| Control | permanent | saline sol. | —/— | i.v. | c | 9 | 129 ± 14 |
| 4-[2-(methylamino)ethyl]-2,6-bis(1,1-dimethylethyl)phenol hydrochloride | permanent | saline sol. | 30/-5+++ | i.v. | c | 8 | 130 ± 16 |
| Control | permanent | saline sol. | —/— | i.v. | c | — | — |
| 4-(1-pyrrolidinomethyl)-2,6-bis(1,1-dimethylethyl)phenol hydrochloride | permanent | saline sol. | 15/5 | i.v. | c | — | testing terminated due to toxicity |
| 4-(1-pyrrolidinomethyl)-2,6-bis(1,1-dimethylethyl)phenol hydrochloride | permanent | saline sol. | 5/5 | i.v. | c | — | testing terminated due to toxicity |
| Control | temporary | saline sol. | —/— | i.v. | d | 6 | 123 ± 14 |
| 4-[(dipropylamino)methyl]-2,6-bis(1,1-dimethylethyl)phenol hydrochloride | temporary | saline sol. | 20/5 | i.v. | d | 6 | 143 ± 12 |
| Control | permanent | saline sol. | —/— | i.v. | c | 8 | 142 ± 7 |
| 4-[(methylamino)methyl]-2,6-bis(1,1-dimethylethyl)phenol hydrochloride | permanent | saline sol. | 50/10 | i.v. | c | 8 | 76 ± 12 |
| Control | permanent | saline sol. | —/— | i.v. | c | 14 | 145 ± 12 |
| 4-[(methylamino)methyl]-2,6-bis(1,1-dimethylethyl)phenol hydrochloride | permanent | saline sol. | 10/10 | i.v. | c | 10 | 128 ± 11 |
| Control | permanent | saline sol. | — | i.v. | e | 5 | 140 ± 23 |
| 4-[(methylamino)methyl]-2,6-bis(1,1-dimethylethyl)phenol hydrochloride | permanent | saline sol. | 50 | i.v. | e | 5 | 123 ± 18 |
| Control | permanent | saline sol. | —/— | i.v. | c | 8 | 148 ± 9 |
| 4-[(methylamino)methyl]-2,6-bis(1,1-dimethylethyl)phenol hydrochloride | permanent | saline sol. | 20/10 | i.v. | c | 6 | 90 ± 18 |
| Control | permanent | saline sol. | —/— | i.v. | c | 7 | 133 ± 16 |
| 4-[(methylamino)methyl]-2,6-bis(1,1-dimethylethyl)phenol hydrochloride | permanent | saline sol. | 20/5 | i.v. | c | 9 | 112 ± 7 |
| Control | permanent | saline sol. | —/— | i.v. | c | 9 | 172 ± 19 |
| 4-[(ethylamino)methyl]-2,6-bis(1,1-dimethylethyl)phenol hydrochloride | permanent | saline sol. | 20/5 | i.v. | c | 8 | 122 ± 12 |
| Control | temporary | saline sol. | —/— | i.v. | f | 15 | 128 ± 17 |
| 4-[(ethylamino)methyl]-2,6-bis(1,1-dimethylethyl)phenol hydrochloride | temporary | saline sol. | 10/5 | i.v. | f | 10 | 74 ± 8 |
| Control | permanent | saline sol. | —/— | i.v. | c | — | — |
| 4-[2-(methylamino)ethyl]-2-(1,1-dimethylethyl)phenol hydrochloride | permanent | saline sol. | 30/7.5 | i.v. | c | — | testing terminated due to toxicity and hypothermia |
| Control | temporary | 10% DMSO in saline sol. | —/— | i.v. | d | 12 | 106 ± 15 |
| 4-[1-(ethylamino)ethyl]- | temporary | 10% DMSO in | 10/5-++ | i.v. | d | 14 | 92 ± 10 |

TABLE III-continued

Prevention of Ischemia-Induced Cell Damage
Caused by Middle Cerebral Artery Occlusion

| Compound/Control | Method of Occlusion | Vehicle | Dose* | Method of Admin. | Time of Admin.** | No. of Rats | Infarct Volume (mm)$^3$ |
|---|---|---|---|---|---|---|---|
| 2,6-bis(1,1-dimethylethyl)-phenol hydrochloride | | saline sol. | | | | | |

*compound - mg/kg rat weight (i.p. and i.v. single dose) or mg/kg rat weight/hour (i.v. continuous dose); compound dissolved in vehicle prior to administration.
control - same volume of vehicle administered as the volume (active ingredient plus vehicle) administered to the test animal.
**Times of administration are as follows:
a = single dose administered intraperitoneally 15 minutes before middle cerebral artery clamping. single dose administered intraperitoneally 15 minutes before clamp removal and continuous dose administered intravenously immediately upon clamp removal for the next 24 hours.
b = single dose administered intraperitoneally 15 minutes after middle cerebral artery clamping. single dose administered intraperitoneally 15 minutes before clamp removal and continuous dose administered intravenously immediately upon clamp removal for the next 24 hours.
c = single dose administered intravenously 15 minutes before middle cerebral artery occlusion and continuous dose administered intravenously for the next 24 hours.
d = single dose administered intravenously 15 minutes before clamp removal and continuous dose administered intravenously immediately upon clamp removal for the next 24 hours.
e = single dose administered intravenously 10 minutes before occlusion.
f = single dose administered intraveneously one hour after middle cerebral artery clamping. single dose administered intraveneously immediately upon clamp removal for the next 24 hours.
$^+$ rats fasted overnight prior to ischemic event.
$^{++}$ higher doses were toxic in this model.
$^{+++}$ dose of 50/10 produced severe hypothermia.

Compounds of formula II have also been shown to prolong the lifespan of dystrophic mammals as demonstrated in the following test system.

MUSCULAR DYSTROPHY ANIMAL MODEL

Dystrophic mice (dy/dy) were obtained from Jackson Laboratories after weaning (approximately 21 days) and treatment with the compound shown in Table IV was begun at the first sign of dystrophy. The compound was administered in the diet and lifespan was measured during the course of treatment. The food and water sources were located in different parts of the cage requiring the animals to walk from the food source to the water source to survive. The results are shown in Table IV.

TABLE IV

Life Span Measurements of Dystrophic Mice

| Treatment | No. of Mice | Wgt % of Compound in Diet | Average Life Span (days) |
|---|---|---|---|
| Control | 7 | — | 73 |
| 4-[(dimethylamino)-methyl]-2,6-bis(1,1-dimethylethyl)phenol | 8 | 0.03 | 120 |

As noted above, the compounds of formulae I and II are physiologically active thereby lending themselves to the valuable therapeutic methods claimed herein. These methods include administering to a mammal in need thereof an effective amount of one or more compounds of formulae I and II sufficient for the therapeutic or prophylactic intervention desired. The compounds can be administered by a variety of routes including the oral, rectal, transdermal, subcutaneous, intravenous, intramuscular or intranasal routes. The oral and intravenous routes of administration are preferred. No matter what route of administration is chosen, such administration is accomplished by means of pharmaceutical compositions which are prepared by techniques well known in the pharmaceutical sciences.

In making the pharmaceutical compositions, one or more active ingredients will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline solution, syrup, methylcellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. The compositions may be formulated so as to provide rapid, sustained or delayed release of the active ingredient after administration to the patient by employing procedures well known in the art.

The compositions are formulated, preferably in a unit dosage form, such that each dosage contains from about 5 to about 500 mg, more usually about 25 to about 300 mg, of the active ingredient. The term "unit dosage form" refers to physically discrete units suitable as unitary dosages for human subjects and other mammals, each unit containing a predetermined quantity of active material calculated to produce the desired therapeutic or prophylactic effect, in association with one or more suitable pharmaceutical diluents, excipients or carriers.

The compounds of the present invention are effective over a wide dosage range for the indications for which they are administered. Thus, as used herein, the term "effective amount" refers to a dosage range of from about 0.5 to about 500 mg/kg of body weight per day. In the treatment of adult humans, the range of about 1 to about 100 mg/kg, in single or divided doses, is preferred. However, it will be understood that the amount of the compound actually administered will be determined by a physician, in the light of the relevant circumstances including the condition to be treated, the choice of compound to be administered, whether prophylactic or therapeutic effect is desired, the chosen route of administration, the age, weight, and response of the individual patient, and the severity of the patient's symptoms, and therefore the above dosage ranges are not intended to limit the scope of the invention in any way.

The following formulation examples may employ as active ingredients any of the compounds of formulae I or II. The examples are illustrative only and are not intended to limit the scope of the invention in any way.

EXAMPLE 1

Hard gelatin capsules are prepared using the following ingredients:

|  | Quantity (mg/capsule) |
|---|---|
| 4-[(dimethylamino)methyl]-2,6-bis(1,1-dimethylethyl)-phenol hydrochloride | 250 |
| Starch dried | 200 |
| Magnesium stearate | 10 |

The above ingredients are mixed and filled into hard gelatin capsules in 460 mg quantities.

EXAMPLE 2

A tablet formula is prepared using the ingredients below:

|  | Quanity (mg/tablet) |
|---|---|
| 4-[(ethylamino)methyl]-2,6-bis(1,1-dimethylethyl)-phenol hydrochloride | 250 |
| Cellulose, microcrystalline | 400 |
| Silicon dioxide, fumed | 10 |
| Stearic acid | 5 |

The components are blended and compressed to form tablets each weighing 665 mg.

EXAMPLE 3

An aerosol solution is prepared containing the following components:

|  | Weight % |
|---|---|
| 4-[2-(dimethylamino)ethyl]-2,6-bis(1,1-dimethylethyl)-phenol | 0.25 |
| Ethanol | 29.75 |
| Propellant 22 (Chlorodifluoromethane) | 70.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

EXAMPLE 4

Tablets each containing 60 mg of active ingredient are made up as follows:

|  |  |
|---|---|
| 4-[(dimethylamino)methyl]-2,6-bis(1,1-dimethylethyl)-phenol | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°-60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed by a tablet machine to yield tablets each weighing 150 mg.

EXAMPLE 5

Capsules each containing 80 mg of medicament are made as follows:

|  |  |
|---|---|
| 4-[(methylamino)methyl]-2,6-bis(1,1-dimethylethyl)-phenol hydrochloride | 80 mg |
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

EXAMPLE 6

Suppositories each containing 225 mg of active ingredient are made as follows:

|  |  |
|---|---|
| 4-[2-(methylamino)ethyl]-2,6-bis(1,1-dimethylethyl)-phenol hydrochloride | 225 mg |
| Saturated fatty acid glycerides to | 2,000 mg |

The active ingredient is passed through a No. mesh U.S. sieve and suspended in the saturated fatty acid glycerides previously melted using the minimum heat necessary. The mixture is then poured into a suppository mold of nominal 2 g capacity and allowed to cool.

EXAMPLE 7

Suspensions each containing 50 mg of medicament per 5 ml dose are made as follows:

|  |  |
|---|---|
| 4-[(dimethylamino)methyl]-2,6-bis(1,1-dimethylethyl)-phenol | 50 mg |
| Sodium carboxymethylcellulose | 50 mg |
| Syrup | 1.25 ml |
| Benzoic acid solution | 0.10 ml |
| Flavor | q.v. |
| Color | q.v. |
| Purified water to | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

EXAMPLE 8

Capsules each containing 150 mg of medicament are made as follows:

| | |
|---|---|
| 4-[(dimethylamino)methyl]-2,6-bis(1,1-dimethylethyl)-phenol methanesulfonate | 150 mg |
| Starch | 164 mg |
| Microcrystalline cellulose | 164 mg |
| Magnesium stearate | 22 mg |
| Total | 500 mg |

The active ingredient, cellulose, starch and magnesium stearate are blended, passed through a No. 45 mesh U.S. sieve, and filled into hard gelatin capsules in 500 mg quantities.

We claim:

1. A method of treating inflammation and arthritis in mammals which comprises administering to said mammal an effective amount of a compound, or a pharmaceutically acceptable salt thereof, of formula (I)

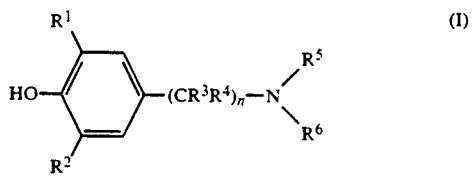

wherein:

$R^1$ and $R^2$ are each independently hydrogen, $C_1$-$C_6$ alkyl, $C_1$-$C_6$ alkoxy or

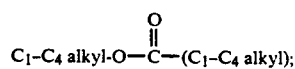

$C_1$-$C_4$ alkyl-O—C—($C_1$-$C_4$ alkyl);

$R^3$ and $R^4$ are each independently hydrogen or $C_1$-$C_4$ alkyl;

n is an integer from 1 to 4, both inclusive; and $R^5$ and $R^6$ are defined to be either:

(A) $R^5$ and $R^6$ are each independently hydrogen, $C_1$-$C_8$ alkyl, $C_3$-$C_8$ cycloalkyl, $C_2$-$C_8$ alkenyl, $C_2$-$C_8$ alkynyl, —$(CH_2)_qOR^7$, —$(CH_2)_qN(R^7R^8)$ or —$(CH_2)_qSR^7$, where q is an integer form 1 to 6, both inclusive, and $R^7$ and $R^8$ are each independently hydrogen or $C_1$-$C_4$ alkyl; or (B) one of $R^5$ and $R^6$ is as defined in (A) above and the other is

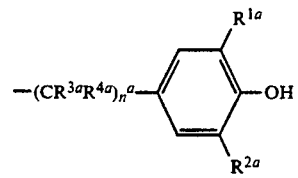

wherein $n^a$, $R^{1a}$, $R^{2a}$, $R^{3a}$ and $R^{4a}$ are the same substituent as n, $R^1$, $R^2$, $R^3$ and $R^4$, respectively.

2. The method of claim 1 which employs a compound of formula I, or a pharmaceutically acceptable salt thereof, wherein $R^1$, $R^2$, $R^3$, $R^4$, and n are as defined in claim 1 and $R^5$ and $R^6$ are defined to be either:

A) $R^5$ and $R^6$ are each independently hydrogen, $C_1$-$C_6$ alkyl, $C_2$-$C_6$ alkenyl, $C_2$-$C_6$ alkynyl, —$(CH_2)_qOH$, —$(CH_2)_qNH_2$, —$(CH_2)_qNH(C_1$-$C_4$ alkyl), —$(CH_2)_qN(C_1$-$C_4$ alkyl)$_2$ or —$(CH_2)_qS(C_1$-$C_4$ alkyl, where q is as defined in claim 1, or B) one of $R^5$ or $R^6$ immediately above and the other is

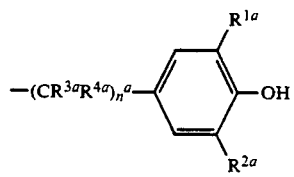

wherein $n^a$, $R^{1a}$, $R^{2a}$, $R^{3a}$ and $R^{4a}$ are the same substituent as n, $R^1$, $R^2$, $R^3$ and $R^4$, respectively.

3. The method of claim 2 which employs a compound of formula I, or a pharmaceutically acceptable salt thereof, wherein $R^1$ and $R^2$ are either both, 1,1-dimethylethyl or one of $R^1$ and $R^2$ is hydrogen and the other is 1,1-dimethylethyl, n is an integer from 1 to 4, both inclusive, $R^3$ and $R^4$ are hydrogen, and $R^5$ and $R^6$ are each independently hydrogen or $C_1$-$C_4$ alkyl.

4. The method of claim 3 wherein the compound employed is 4-[(dimethylamino)methyl]-2,6-bis(1,1-dimethylethyl)phenol or a pharmaceutically acceptable salt thereof.

5. The method of claim 4 wherein the pharmaceutically acceptable salt thereof is the hydrochloride salt.

6. The method of claim 4 wherein the pharmaceutically acceptable salt thereof is the methanesulfonate salt.

7. The method of claim 3 wherein the compound employed is 4-[2-(methylamino)ethyl]-2,6-bis(1,1-dimethylethyl)phenol or a pharmaceutically acceptable salt thereof.

8. The method of claim 7 wherein the pharmaceutically acceptable salt thereof is the hydrochloride salt.

9. The method of claim 3 wherein the compound employed is 4-[(methylamino)methyl]-2,6-bis(1,1-dimethylethyl)phenol or a pharmaceutically acceptable salt thereof.

10. The method of claim 9 wherein the pharmaceutically acceptable salt thereof is the hydrochloride salt.

11. The method of claim 3 wherein the compound employed is 4-[(ethylamino)methyl]-2,6-bis(1,1-dimethylethyl)phenol or a pharmaceutically acceptable salt thereof.

12. The method of claim 11 wherein the pharmaceutically acceptable salt thereof is the hydrochloride salt.

13. The method of claim 3 wherein the compound employed is 4-[2-(methylamino)ethyl]-2-(1,1-dimethylethyl)phenol or a pharmaceutically acceptable salt thereof.

14. The method of claim 13 wherein the pharmaceutically acceptable salt thereof is the hydrochloride salt.

* * * * *